(12) United States Patent
Long

(10) Patent No.: US 9,301,848 B2
(45) Date of Patent: Apr. 5, 2016

(54) MODULAR GLENOID PROSTHESIS

(71) Applicant: Jack F Long, Warsaw, IN (US)

(72) Inventor: Jack F Long, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 13/896,455

(22) Filed: May 17, 2013

(65) Prior Publication Data

US 2013/0253656 A1    Sep. 26, 2013

Related U.S. Application Data

(62) Division of application No. 12/953,519, filed on Nov. 24, 2010, now Pat. No. 8,465,548.

(51) Int. Cl.
*A61F 2/40* (2006.01)
*A61F 2/30* (2006.01)

(52) U.S. Cl.
CPC ........... *A61F 2/4081* (2013.01); *A61F 2/30749* (2013.01); *A61F 2002/305* (2013.01); *A61F 2002/30378* (2013.01); *A61F 2002/30387* (2013.01); *A61F 2002/30604* (2013.01); *A61F 2002/30736* (2013.01); *A61F 2002/30878* (2013.01); *Y10T 29/49826* (2015.01)

(58) Field of Classification Search
CPC ..... A61F 2/40; A61F 2/38; A61F 2220/0033; A61F 2/4081
USPC ................................ 623/16.11, 19.11–19.14
See application file for complete search history.

(56) References Cited

U.S. PATENT DOCUMENTS

| | | | |
|---|---|---|---|
| 3,061,977 | A | 11/1962 | Schmidt |
| 3,694,820 | A | 10/1972 | Scales |
| 3,837,008 | A | 9/1974 | Bahler |
| 3,855,638 | A | 12/1974 | Pilliar |
| 3,916,451 | A | 11/1975 | Buechel |
| 4,040,130 | A | 8/1977 | Laure |
| 4,042,980 | A | 8/1977 | Swanson |
| 4,045,825 | A | 9/1977 | Stroot |
| 4,045,826 | A | 9/1977 | Stroot |
| 4,106,128 | A | 8/1978 | Greenwald |
| 4,172,296 | A | 10/1979 | D'Errico |
| 4,180,871 | A | 1/1980 | Hamas |
| 4,524,467 | A | 6/1985 | DeCarlo, Jr. |
| 4,550,450 | A | 11/1985 | Kinnett |
| D285,968 | S | 9/1986 | Kinnett |

(Continued)

FOREIGN PATENT DOCUMENTS

| | | |
|---|---|---|
| DE | 102006041550 | 11/2007 |
| DE | 102008021110 A1 | 10/2009 |

(Continued)

OTHER PUBLICATIONS

Translation of FR2652498A1—Inventor: Michael Columbier, Date of Publ. Oct. 4, 1989.

(Continued)

*Primary Examiner* — Jason-Dennis Stewart

(57) ABSTRACT

A method of assembling a glenoid assembly. The method includes selecting a base from a plurality of bases. At least one of the plurality of bases has a size different than a size of one of the other of the plurality of bases. The selected base is coupled to an articulating member and the selected base is locked to the articulating member via a locking mechanism.

5 Claims, 5 Drawing Sheets

(56) References Cited

U.S. PATENT DOCUMENTS

| | | |
|---|---|---|
| 4,693,723 A | 9/1987 | Gabard |
| 4,695,282 A | 9/1987 | Forte |
| 4,795,468 A | 1/1989 | Hodorek |
| 4,865,025 A | 9/1989 | Buzzi |
| 4,865,605 A | 9/1989 | Dines |
| 4,919,670 A | 4/1990 | Dale |
| 4,936,853 A | 6/1990 | Fabian |
| 4,964,865 A | 10/1990 | Burkhead |
| 4,986,833 A | 1/1991 | Worland |
| 4,987,904 A | 1/1991 | Wilson |
| 5,030,219 A | 7/1991 | Matsen, III |
| 5,032,132 A | 7/1991 | Matsen, III |
| 5,047,058 A | 9/1991 | Roberts |
| 5,080,673 A | 1/1992 | Burkhead |
| 5,108,446 A | 4/1992 | Wagner |
| 5,150,304 A | 9/1992 | Berchem |
| 5,197,465 A | 3/1993 | Montgomery |
| 5,201,882 A | 4/1993 | Paxson |
| 5,304,181 A | 4/1994 | Caspari |
| 5,314,479 A | 5/1994 | Rockwood, Jr. |
| 5,344,461 A | 9/1994 | Phlipot |
| 5,358,526 A | 10/1994 | Tornier |
| 5,370,693 A | 12/1994 | Kelman |
| 5,387,241 A | 2/1995 | Hayes |
| 5,437,677 A | 8/1995 | Shearer |
| 5,458,637 A | 10/1995 | Hayes |
| 5,474,559 A | 12/1995 | Bertin |
| 5,486,180 A | 1/1996 | Dietz |
| 5,489,309 A | 2/1996 | Lackey |
| 5,489,310 A | 2/1996 | Mikhail |
| 5,496,324 A | 3/1996 | Barnes |
| 5,507,821 A | 4/1996 | Sennwald |
| 5,554,158 A | 9/1996 | Vinciguerra |
| 5,593,441 A | 1/1997 | Lichtenstein |
| 5,593,448 A | 1/1997 | Dong |
| 5,601,563 A | 2/1997 | Burke |
| 5,665,090 A | 9/1997 | Rockwood |
| 5,702,447 A | 12/1997 | Walch |
| 5,718,360 A | 2/1998 | Green |
| 5,723,018 A | 3/1998 | Cyprien |
| 5,743,915 A | 4/1998 | Bertin |
| 5,769,855 A | 6/1998 | Bertin |
| 5,779,710 A | 7/1998 | Matsen, III |
| 5,782,924 A | 7/1998 | Johnson |
| 5,800,551 A | 9/1998 | Williamson |
| 5,853,415 A | 12/1998 | Bertin |
| 5,860,981 A | 1/1999 | Bertin |
| 5,879,401 A | 3/1999 | Besemer |
| 5,908,424 A | 6/1999 | Bertin |
| 5,928,285 A | 7/1999 | Bigliani |
| 5,976,145 A | 11/1999 | Kennefick, III |
| 6,045,582 A | 4/2000 | Prybyla |
| 6,096,084 A | 8/2000 | Townley |
| 6,139,581 A | 10/2000 | Engh |
| 6,197,062 B1 | 3/2001 | Fenlin |
| 6,197,063 B1 | 3/2001 | Dews |
| 6,206,925 B1 | 3/2001 | Tornier |
| 6,228,119 B1 | 5/2001 | Ondrla |
| 6,228,900 B1 | 5/2001 | Shen |
| 6,245,074 B1 | 6/2001 | Allard |
| 6,281,264 B1 | 8/2001 | Salovey |
| 6,364,910 B1 | 4/2002 | Shultz |
| 6,368,353 B1 | 4/2002 | Arcand |
| 6,379,386 B1 | 4/2002 | Resch |
| 6,406,495 B1 | 6/2002 | Schoch |
| 6,488,715 B1 | 12/2002 | Pope |
| 6,514,287 B2 | 2/2003 | Ondrla |
| 6,620,197 B2 | 9/2003 | Maroney |
| 6,673,115 B2 | 1/2004 | Resch |
| 6,676,705 B1 | 1/2004 | Wolf |
| 6,679,916 B1 | 1/2004 | Frankle |
| 6,699,289 B2 | 3/2004 | Iannotti |
| 6,699,290 B1 | 3/2004 | Wack et al. |
| 6,783,549 B1 | 8/2004 | Stone |
| 6,875,234 B2 | 4/2005 | Lipman |
| 6,893,702 B2 | 5/2005 | Takahashi |
| 6,896,702 B2 | 5/2005 | Collazo |
| 6,899,736 B1 | 5/2005 | Rauscher |
| 6,911,047 B2 | 6/2005 | Rockwood, Jr. |
| 6,942,699 B2 | 9/2005 | Stone |
| 6,953,478 B2 | 10/2005 | Bouttens |
| 7,033,396 B2 | 4/2006 | Tornier |
| 7,051,451 B2 | 5/2006 | Augostino |
| 7,090,677 B2 | 8/2006 | Fallin |
| 7,160,328 B2 | 1/2007 | Rockwood, Jr. |
| 7,160,331 B2 | 1/2007 | Cooney, III |
| 7,169,184 B2 | 1/2007 | Dalla Pria |
| 7,175,663 B1 | 2/2007 | Stone |
| 7,175,665 B2 | 2/2007 | German |
| 7,204,854 B2 | 4/2007 | Guederian |
| 7,329,284 B2 | 2/2008 | Maroney |
| 7,527,631 B2 | 5/2009 | Maroney |
| 7,604,665 B2 | 10/2009 | Iannotti |
| 7,608,109 B2 | 10/2009 | Dalla Pria |
| 7,621,961 B2 | 11/2009 | Stone |
| 7,625,408 B2 | 12/2009 | Gupta |
| 7,753,959 B2 | 7/2010 | Berelsman |
| 7,766,969 B2 | 8/2010 | Justin |
| 7,879,275 B2 | 2/2011 | Smith |
| 7,892,287 B2 | 2/2011 | Deffenbaugh |
| 7,896,921 B2 | 3/2011 | Smith |
| 7,918,895 B2 | 4/2011 | Isch |
| 7,922,769 B2 | 4/2011 | Deffenbaugh |
| 7,927,335 B2 | 4/2011 | Deffenbaugh |
| 7,959,680 B2 | 6/2011 | Stone |
| 8,241,365 B2 | 8/2012 | Williams, Jr. |
| 8,425,614 B2 | 4/2013 | Winslow |
| 2001/0011192 A1 | 8/2001 | Ondrla |
| 2001/0018589 A1 | 8/2001 | Muller |
| 2001/0030339 A1 | 10/2001 | Sandhu |
| 2001/0037153 A1 | 11/2001 | Rockwood, Jr. |
| 2002/0004685 A1 | 1/2002 | White |
| 2002/0082702 A1 | 6/2002 | Resch |
| 2002/0095214 A1 | 7/2002 | Hyde |
| 2002/0099445 A1 | 7/2002 | Maroney |
| 2003/0028253 A1 | 2/2003 | Stone |
| 2003/0045883 A1 | 3/2003 | Chow |
| 2003/0055507 A1 | 3/2003 | McDevitt |
| 2003/0065397 A1 | 4/2003 | Hanssen |
| 2003/0097183 A1 | 5/2003 | Rauscher |
| 2003/0114933 A1 | 6/2003 | Bouttens |
| 2003/0125809 A1 | 7/2003 | Iannotti |
| 2003/0149485 A1 | 8/2003 | Tornier |
| 2003/0187514 A1 | 10/2003 | McMinn |
| 2004/0064189 A1 | 4/2004 | Maroney |
| 2004/0122519 A1 | 6/2004 | Wiley |
| 2004/0122520 A1 | 6/2004 | Lipman |
| 2004/0162619 A1 | 8/2004 | Blaylock |
| 2004/0193277 A1 | 9/2004 | Long |
| 2004/0193278 A1 | 9/2004 | Maroney |
| 2004/0220673 A1 | 11/2004 | Pria |
| 2004/0220674 A1 | 11/2004 | Pria |
| 2004/0230312 A1 | 11/2004 | Hanson |
| 2004/0236424 A1 | 11/2004 | Berez |
| 2005/0021148 A1 | 1/2005 | Gibbs |
| 2005/0049709 A1 | 3/2005 | Tornier |
| 2005/0125068 A1 | 6/2005 | Hozack |
| 2005/0171613 A1 | 8/2005 | Sartorius |
| 2005/0261775 A1 | 11/2005 | Baum |
| 2006/0030946 A1 | 2/2006 | Ball |
| 2006/0069443 A1 | 3/2006 | Deffenbaugh |
| 2006/0069444 A1 | 3/2006 | Deffenbaugh |
| 2006/0074353 A1 | 4/2006 | Deffenbaugh |
| 2006/0074430 A1 | 4/2006 | Deffenbaugh |
| 2006/0079963 A1 | 4/2006 | Hansen |
| 2006/0100498 A1 | 5/2006 | Boyce |
| 2006/0100714 A1 | 5/2006 | Ensign |
| 2006/0111787 A1 | 5/2006 | Bailie |
| 2006/0149387 A1 | 7/2006 | Smith |
| 2006/0149388 A1 | 7/2006 | Smith |
| 2006/0161260 A1 | 7/2006 | Thomas |
| 2006/0265079 A1 | 11/2006 | D'Alessio, II |
| 2007/0055380 A1 | 3/2007 | Berelsman |
| 2007/0142917 A1 | 6/2007 | Roche |

(56) References Cited

U.S. PATENT DOCUMENTS

| | | |
|---|---|---|
| 2007/0179624 A1 | 8/2007 | Stone |
| 2007/0219637 A1 | 9/2007 | Berelsman |
| 2007/0219638 A1 | 9/2007 | Jones |
| 2007/0225817 A1 | 9/2007 | Reubelt |
| 2008/0046091 A1 | 2/2008 | Weiss |
| 2008/0140209 A1 | 6/2008 | Iannotti |
| 2008/0208348 A1 | 8/2008 | Fitz |
| 2008/0234820 A1 | 9/2008 | Felt |
| 2009/0125113 A1 | 5/2009 | Guederian |
| 2009/0143865 A1 | 6/2009 | Hassler |
| 2009/0204225 A1 | 8/2009 | Meridew |
| 2009/0281630 A1 | 11/2009 | Delince |
| 2009/0292364 A1 | 11/2009 | Linares |
| 2009/0312839 A1 | 12/2009 | Scheker |
| 2010/0030339 A1 | 2/2010 | Berelsman et al. |
| 2010/0049327 A1 | 2/2010 | Isch |
| 2010/0161065 A1 | 6/2010 | Williams et al. |
| 2011/0035013 A1* | 2/2011 | Winslow et al. ........... 623/19.13 |
| 2011/0106267 A1 | 5/2011 | Grant |

FOREIGN PATENT DOCUMENTS

| | | |
|---|---|---|
| EP | 103246 A1 | 3/1984 |
| EP | 329854 A1 | 8/1989 |
| EP | 339530 A2 | 11/1989 |
| EP | 339530 A3 | 3/1990 |
| EP | 329854 B1 | 11/1992 |
| EP | 538895 A2 | 4/1993 |
| EP | 538895 A3 | 6/1993 |
| EP | 581667 A1 | 2/1994 |
| EP | 776636 A1 | 6/1997 |
| EP | 903127 A2 | 3/1999 |
| EP | 0963742 A1 | 12/1999 |
| EP | 1013246 A1 | 6/2000 |
| EP | 776636 B1 | 9/2000 |
| EP | 1064890 A1 | 1/2001 |
| EP | 1013246 B1 | 10/2003 |
| EP | 903127 A3 | 11/2003 |
| EP | 1402853 A2 | 3/2004 |
| EP | 1064890 B1 | 9/2005 |
| EP | 1402853 A3 | 3/2006 |
| EP | 1639966 A1 | 3/2006 |
| EP | 1639967 A1 | 3/2006 |
| EP | 903127 B1 | 6/2007 |
| EP | 1639966 B1 | 9/2007 |
| EP | 1902689 A1 | 3/2008 |
| EP | 1639967 B1 | 7/2008 |
| EP | 1402853 B1 | 5/2010 |
| EP | 1902689 B1 | 11/2011 |
| FR | 1064890 A | 5/1954 |
| FR | 2578162 A1 | 9/1986 |
| FR | 2579454 A1 | 10/1986 |
| FR | 2652498 A1 | 4/1991 |
| FR | 2683142 A1 | 5/1993 |
| FR | 2695313 A1 | 3/1994 |
| FR | 2704747 A1 | 11/1994 |
| FR | 2755847 A1 | 5/1998 |
| FR | 2776506 A1 | 10/1999 |
| FR | 2825263 A1 | 12/2002 |
| GB | 2297257 A | 7/1996 |
| WO | WO 00/01326 | 1/2000 |
| WO | WO 0134040 A1 | 5/2001 |
| WO | WO 02067821 A2 | 9/2002 |
| WO | WO 03005933 A2 | 1/2003 |
| WO | WO 03030770 A2 | 4/2003 |
| WO | WO 02067821 A3 | 8/2003 |
| WO | WO 03005933 A3 | 10/2003 |
| WO | WO 03030770 A8 | 10/2003 |
| WO | WO 2007096741 A2 | 8/2007 |
| WO | WO 2007096741 A3 | 12/2007 |
| WO | WO 2011098890 A1 | 8/2011 |

OTHER PUBLICATIONS

Translation of FEP0339530—Inventor: Hans Grundel: Date of Publ. Nov. 2, 1989.
Print Out From Espacenet of FR2704747A1—Inventor Didier Capon, et al: Date of Publ Nov. 10, 1994.
Print Out From Espacenet of FR2776505(A1)—Inventor Katz Denis et al, Date of Publ Oct. 1, 1999.
EPO Search Report for (EP09178360) Dated May 12, 2010 (7 Pages).
Biomet Biomodular Low Profile Modular Glenoid, Biomet Corporation, One Page, Available at Least as Early as Nov. 24, 2010.
Biomet Biangular Standard Metal Backed Glenoid, Biomet Corporation, One Page, 1996.
Kirschner Integrated Shoulder System for Hemi & Total Shoulder Arthroplasty, Kirschner Medical Corporation, Two Pages, Available at Least as Early as Nov. 24, 2010.
The Cofield Total Shoulder System, Smith & Nephew Richards, Inc., Two Pages, Available at Least as Early as Nov. 24, 2010.
European Search Report Completed Sep. 10, 1999, Mailed Sep. 17, 1999.
PCT Search Report for PCT/US2011/061347, Dated Feb. 9, 2012, 11 Pages.
PCT Search Report for PCT/US2011/061357, Dated Feb. 3, 2012, 18 Pages.

* cited by examiner

MODULAR GLENOID PROSTHESIS

CROSS-REFERENCE TO RELATED APPLICATION

This is a divisional application of U.S. patent application Ser. No. 12/953519 entitled "MODULAR GLENOID PROSTHESIS and cross reference is made to the following application U.S. patent application Ser. No. 12/953522 entitled "MODULAR GLENOID PROSTHESIS", both of which are incorporated herein by reference.

TECHNICAL FIELD

The present invention relates to a prosthetic glenoid component and particularly to a modular glenoid assembly for attachment to a glenoid surface of a scapula to replace a natural socket of a shoulder and to provide a bearing surface for a head portion of an arm bone or humerus.

BACKGROUND

During the lifetime of a patient, it may be necessary to perform a total shoulder replacement procedure on the patient as a result of, for example, disease or trauma. In a total shoulder replacement procedure, a humeral component having a head portion is utilized to replace the natural head portion of the arm bone or humerus. The humeral component typically has an elongated intramedullary stem which is utilized to secure the humeral component to the patient's humerus. In such a total shoulder replacement procedure, the natural glenoid surface of the scapula is resurfaced or otherwise replaced with a glenoid component which provides a bearing surface for the head portion of the humeral component.

Glenoid components have heretofore been designed which include a number of plastic inserts coupled to metal backings The metal backings are provided to secure the plastic inserts to the glenoid surface of the scapula. However, use of such two-piece glenoid components has a number of drawbacks associated therewith. For example, it is possible over the useful life of the glenoid component for the plastic inserts to separate from the metal backing thereby necessitating replacement of the glenoid component. In addition, over time wear of the plastic insert inherently occurs at the interface between plastic insert and the metal backing It is possible for the plastic insert to wear to a degree which necessitates replacement of the glenoid component. It should be appreciated that in either case, such replacement of the glenoid component requires the patient to again be subjected to a surgical procedure and the subsequent recovery period associated therewith.

In response to the shortcomings associated with two-piece glenoid component designs, a number of one-piece glenoid components have heretofore been designed. In regard to such one-piece designs, a body portion, having a bearing surface defined therein for receiving the head of the humeral component, has a number of attachment pegs integrally formed therewith. The attachment pegs are advanced and thereafter secured into a corresponding number of holes which are drilled in the glenoid surface of the scapula by use of bone cement. An example of such a one-piece glenoid component that is designed to be secured to the scapula by use of bone cement is disclosed in U.S. Pat. No. 5,032,132 issued to Matsen, III et al.

As with the two-piece designs, certain one-piece glenoid components which have heretofore been designed have a number of drawbacks associated therewith. For example, some studies have speculated that it may be desirable to secure artificial components to natural bone structures without the use of bone cement. Glenoid components which have been designed to be secured to the scapula by the use of bone cement generally cannot be secured to the natural glenoid without use of the same.

Many glenoid component designs have been manufactured to address different types of scapular deficiencies. For example, some glenoid components have anchor pegs with flexible fins that are designed to act as barbs when inserted into the scapula. Other designs may utilize glenoid components with a buttress extending from the glenoid to fill larger defects in the natural glenoid. These may also include anchor and/or stabilizing pegs. In other embodiments a vault-filling glenoid may be used to fill a natural glenoid that has severe defects.

However, one problem with even existing modular designs, is that they do not provide the surgeon with the option of using different designs once surgery has started. Also, if a kit was to include all the different sizes and variations, the kit would be quite large and cumbersome to bring into surgery.

Another problem is that glenoid bone quality and surface deterioration varies significantly from patient-to-patient. Therefore, in current designs, having standard peg or buttress or vault locations may not work with specific patients' anatomy. Furthermore, in some embodiments, the surgeon may choose a medial-lateral approach. In that approach, it may be difficult to fit posts and vaults that are designed to be inserted from an overhead position.

SUMMARY

According to one embodiment of the present invention, a kit for making glenoid prosthesis is provided. The kit includes an articulating member having an articulation side and an opposing second side opposing the articulating member. The opposing second side includes a locking mechanism. The kit further includes a plurality of bases. Each of the plurality of bases has an articulating-member facing side and a glenoid attachment side. Each of the plurality of glenoid attachment sides includes at least one glenoid attachment member extending outwardly and is sized and shaped to extend into a patient's glenoid. The glenoid attachment member of one of the plurality of bases differs from the glenoid attachment member of at least one other of the plurality of bases. Each of the plurality of bases includes a locking mechanism sized and shaped to lock each of the plurality of bases to the articulating member.

According to another embodiment of the present invention, the method of assembling a glenoid assembly is provided. A base is selected from a plurality of bases. At least one of the plurality of bases has a size different than a size of one of the other of the plurality of bases. The selected base is coupled to an articulating member. The selected base is locked to the articulating member via a locking mechanism.

According to yet another embodiment of the present invention, a kit for making glenoid prosthesis is provided. The kit includes an articulating member having an articulation side and an opposing second side opposing the articulating member. The opposing second side includes a locking mechanism. The kit further includes a plurality of bases, and each of the plurality of bases has an articulating-member facing side and a glenoid attachment side. Each of the plurality of glenoid attachment sides differs from the glenoid attachment side of at least one other of the plurality of bases. Each of the plurality of bases includes a locking mechanism sized and shaped to lock each of the plurality of bases to the articulating member.

Additional features of the present invention will become apparent to those skilled in the art upon consideration of the following detailed description of preferred embodiments exemplifying the best mode of carrying out the invention as presently perceived.

DETAILED DESCRIPTION OF THE DRAWINGS

Figure 1:
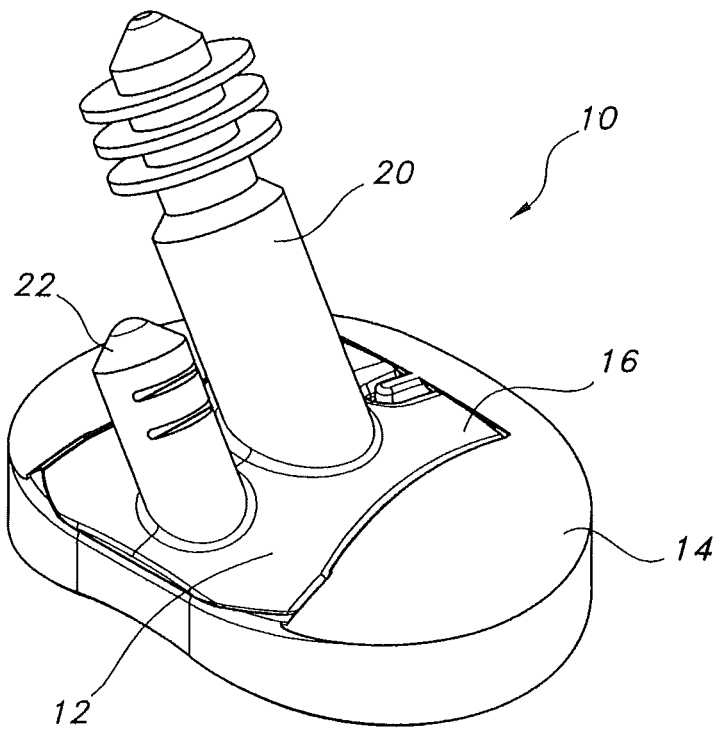
FIG. 1 is a perspective view of a glenoid assembly according to one embodiment of the present invention.
Figure 2:
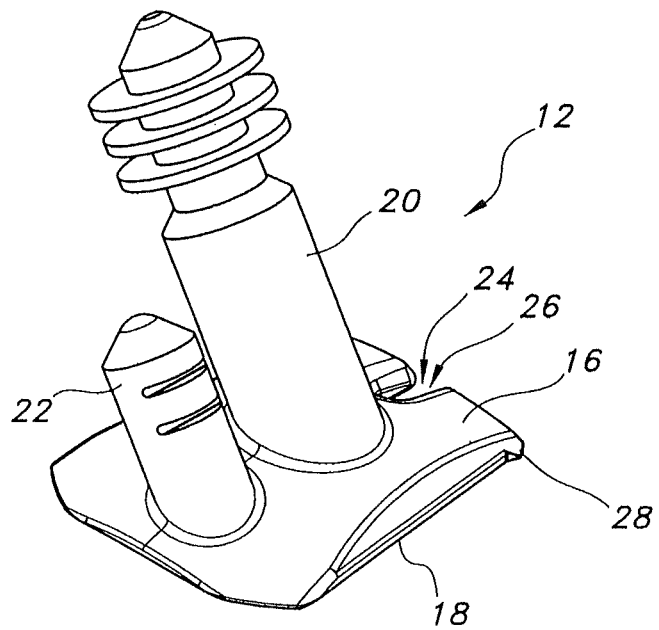
FIG. 2 is a perspective view of a base of the glenoid assembly of FIG. 1.

A modular glenoid assembly 10 is provided in accordance with the present invention. FIG. 1 shows glenoid assembly 10 including a base 12 and an articulation member 14. The base 12 and articulation member 14 are locked in a fixed relationship. As shown in FIGS. 1 and 2, the base 12 includes a first side 16 and a second side 18. The first side 16 includes a finned anchor peg 20 and a cemented peg 22 sized and shaped to attach to a glenoid as will be described further below. Although in this embodiment the base 12 includes a single finned anchor peg 20 and a single cemented peg 22, it should be understood that in other embodiments, there may be differing numbers of pegs 20, 22. Furthermore, the base 12 may include other types of attachment members such as pins, screws, wedge-shaped fillers, spikes. The second side 18 of the base 12 is generally flat and is sized and shaped to abut the articulation member 14.

The base 12 also includes locking features 24. The locking features 24 in the embodiment illustrated in FIGS. 1 and 2 include a locking recess 26 and a pair of locking protrusions 28. These will be described below in further detail.

Figure 3:
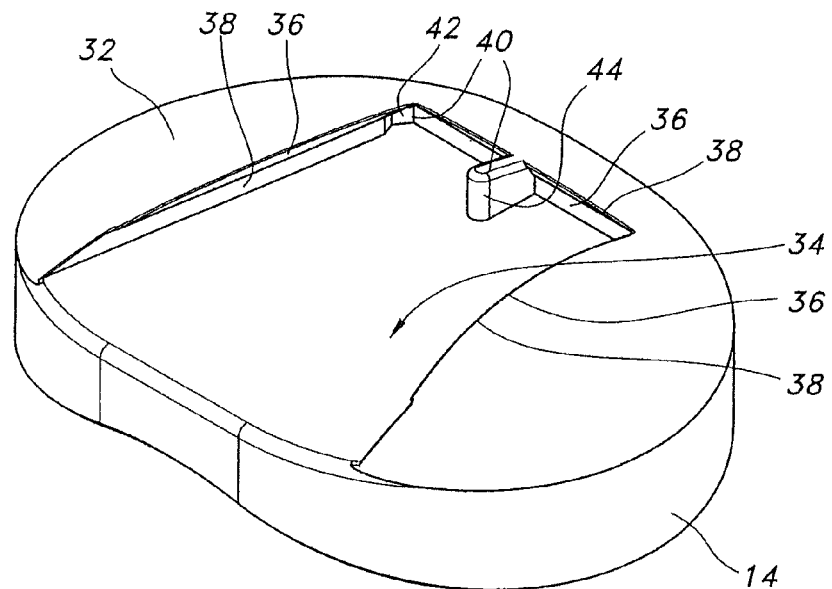
FIG. 3 is a perspective view of an articulating member of the glenoid assembly of FIG. 1.

Turning now to FIGS. 1 and 3, the articulation member 14 will be further described. The articulation member 14 includes an articulation side 30 and an attachment side 32. The attachment side 32 is sized and shaped to receive the second side 18 of the base 12. The attachment side 32 includes an opening 34 defined on three sides by walls 36 of the attachment side 32. The fourth side is open, to allow the base 12 to slide into the articulating member 14. The top of the three walls 36 may include a lip 38 that extends out into the recess 34. The lip 38 exerts pressure against the base 12 and keeps the base from falling out of the articulating member 14.

The articulating member 14 further includes locking features 40 sized and shaped to engage the locking features 24 of the base 12. As shown in this embodiment, the locking features 40 include a pair of wall recesses 42. The pair of wall recesses 42 engages the pair of locking protrusions 28 of the base 12 (FIG. 2) so as to lock the base 12 to the articulating member 14. As the base 12 is slid in through the open side 38, the locking protrusions 28 will snap lock into place in the recesses 42. In this embodiment, the locking features 24 of the base 12 also includes the locking recess 26 that corresponds to a projection 44 in the articulating member 14. The projection 44 extends out into the recess 34 of the articulation member 14 and engages the locking recess 26 in a snap-locked configuration. Other types of locking arrangements such as tapers, locking rings, and other known locking mechanisms may be used.

Figure 4:
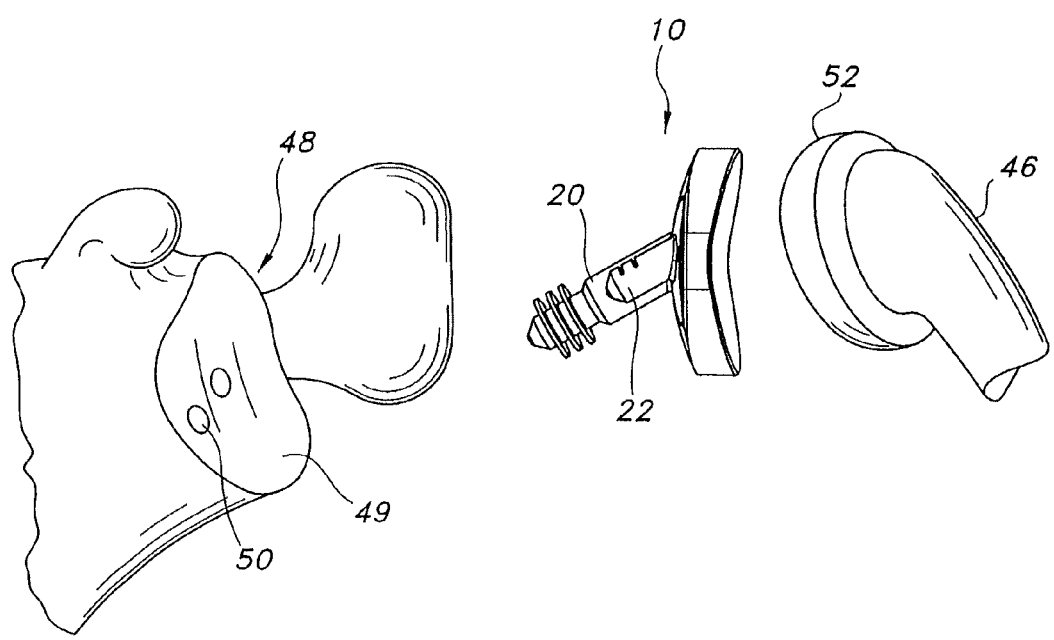
FIG. 4 is a perspective view of the modular glenoid assembly of FIG. 1 positioned between a glenoid surface of a scapula and a humeral component.

Turning now to FIG. 4, the glenoid assembly 10 is shown with respect to a humerus 46 and a scapula 48. Glenoid assembly 10 is designed to be attached to glenoid surface 49 of scapula 48 to replace the natural glenoid surface. As shown, the finned anchor peg 20 and cemented peg 22 correspond to holes 50 drilled into the glenoid surface 49. The finned anchor peg 20 and cemented peg 22 will be placed in the holes 50, locking the glenoid assembly 10 to the glenoid surface 49.

The articulation side 30 of the articulation member 14 is smooth and will articulate with the head portion 52 of the humeral component 46. In some embodiments, the head portion 52 may also be an implant. In other embodiments, the head portion 52 may be the natural humeral head.

FIG. 4 illustrates an embodiment in which the glenoid assembly 10 is assembled prior to the glenoid assembly 10 being implanted into the prepared glenoid 49. However, in other embodiments, the prepared glenoid 49 may be prepared as described above. Then, the base 12 is inserted into the holes 50 of the prepared glenoid 49. The opening 34 of the articulating member 14 is then slid onto the base 12, locking the base 12 and the articulating member 14.

Figure 5:
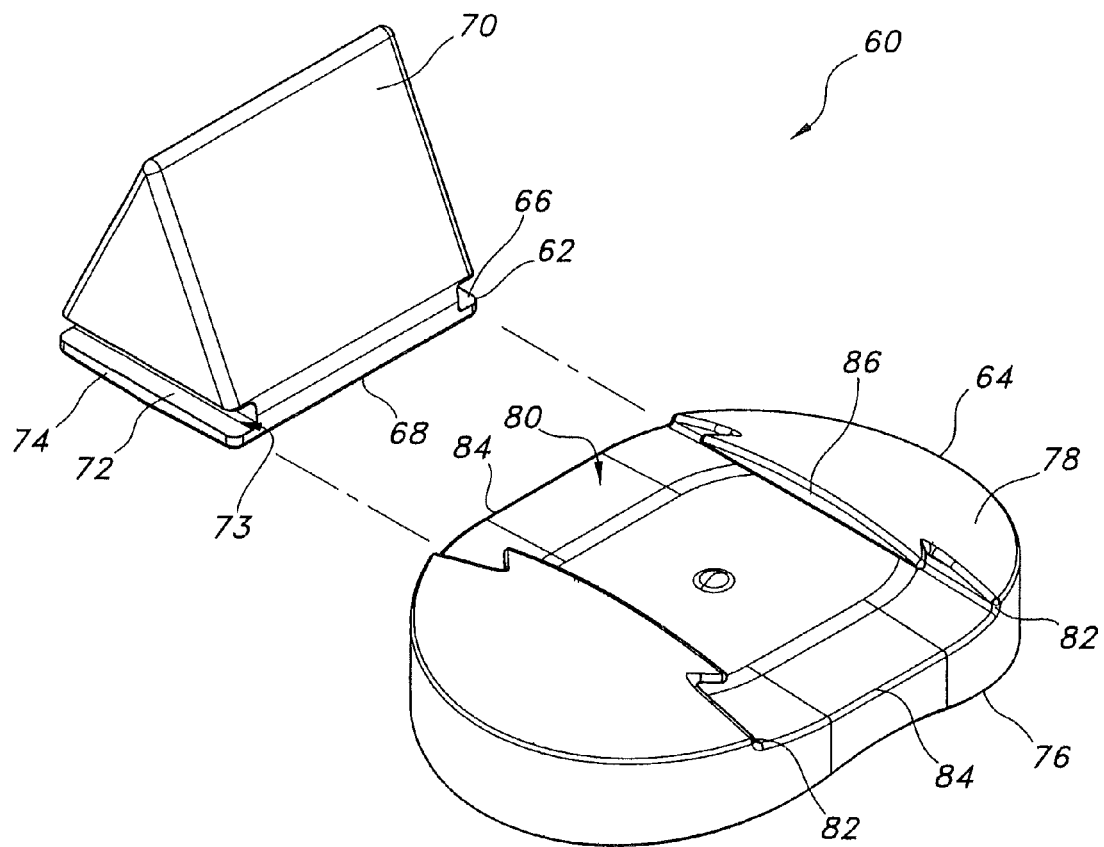
FIG. 5 is a perspective view of a glenoid assembly according to another embodiment of the present invention.

Turning now to FIG. 5, another embodiment of the present invention is illustrated. In this embodiment, a glenoid assembly 60 includes a base 62 and an articulating member 64. A modular glenoid assembly 60 is provided in accordance with the present invention. FIG. 5 shows glenoid assembly 60 including a base 62 and an articulation member 64. The base 62 and articulation member 64 are locked in a fixed relationship. As shown in FIG. 5, the base 62 includes a first side 66 and a second side 68. The first side 66 includes a wedge-shaped filler 70 sized and shaped to attach to a glenoid. Similar to how was described in the previous embodiment, a glenoid is prepared to fit the wedge-shaped filler 70. Although in this embodiment the base 62 includes a wedge-shaped filler 70, it should be understood that in other embodiments, there may be other attachment-type mechanisms, such as cemented pegs, finned anchor pegs, pins, screws, and/or spikes. The second side 68 of the base 62 is generally flat and is sized and shaped to abut the articulation member 14.

The base 62 also includes locking features 72. The locking features 72 in the embodiment illustrated in FIG. 5 include a recess 73 defined by the wedge-shaped filler 70 and a lip 74 that extends outwardly. The recess 73 and lip 74 will be described further below.

Turning now to the articulation member 64, the articulation member 64 includes an articulation side 76 and an attachment side 78. The attachment side 78 is sized and shaped to receive the second side 68 of the base 62. The attachment side 78 includes an opening 80 defined on two sides by walls 82 of the attachment side 78. The other two sides 84 oppose one another and are open, to allow the base 62 to slide into the articulating member 64. The top of the two walls 82 may include a projection 86 that extends out into the recess 73. The projection 86 exerts pressure against the base 62 and keeps the base from falling out of the articulating member 64. In use, the base 62 is slid into one of the open sides 84 and the lip 74 engages the side walls 82, while the projection 86 fits within the recess 73 of the base 62. In some embodiments, there may be three side walls 82, not just two and only one open side 84. Also, other types of locking arrangements such as tapers, locking rings, and other known locking mechanisms may be used.

Figure 6:
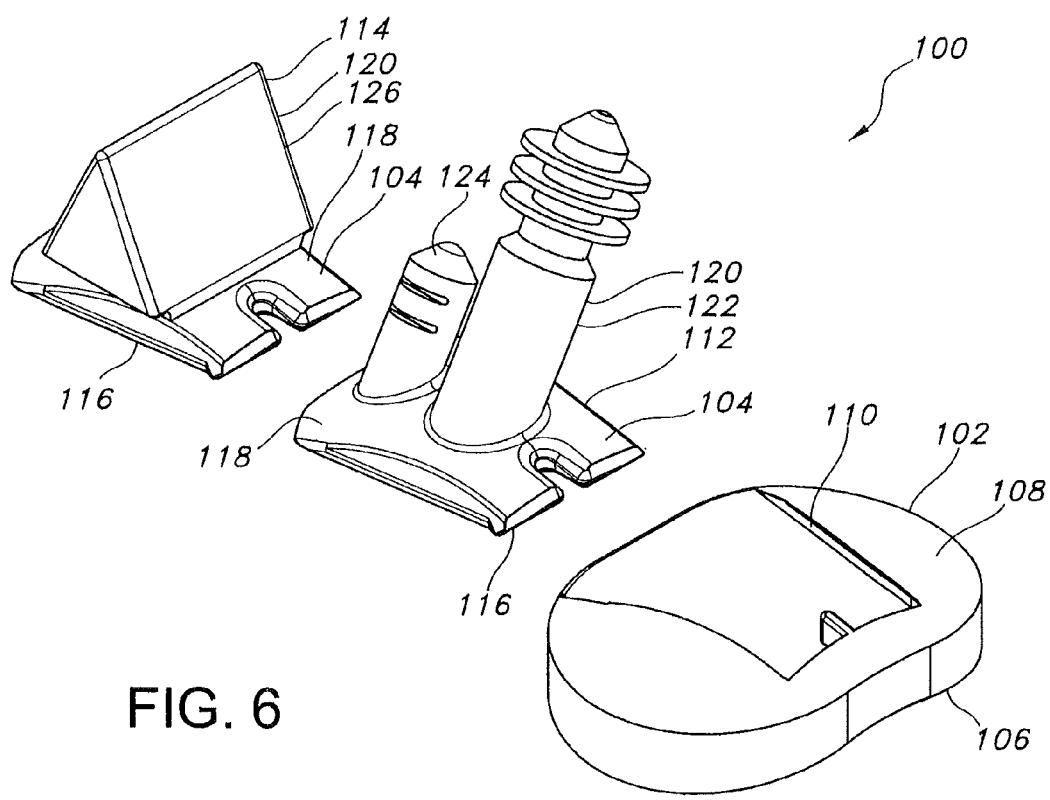
FIG. 6 is an illustration showing a kit for making a modular glenoid assembly according to one embodiment of the present invention.

Turning now to FIG. 6, a kit 100 for modular glenoid prosthesis is shown. The kit includes an articulating member 102 and a plurality of bases 104. The articulating member 102 includes an articulating side 106 and an opposing second side 108. The opposing second side includes a locking mechanism 110. In this embodiment, the locking mechanism 110 is the same as that described in FIGS. 1-4. In other embodiments, the locking mechanism 110 may be of the same type as described in FIG. 5.

The plurality of bases 104 includes a pegged base 112 and a wedge-shaped filler base 114. Each of the plurality of bases 104 have an articulating-member facing side 116 and a glenoid attachment side 118, which includes at least one glenoid attachment member 120 extending outwardly and sized and shaped to extend into a patient's glenoid. The pegged base 112 has a glenoid attachment member 120 that includes a finned anchor peg 122 and a cemented peg 124. The wedge-shaped filler base 114 includes a glenoid attachment member 120 that is a wedge-shaped filler 126. Other glenoid attachment members 120 may also be included, such as screws, pins, spikes, and other numbers of pegs 122, 124. Each of the plurality of bases 104 also includes a locking mechanism 128. The locking mechanism 128 is of the type described in FIGS. 1-4. In other embodiments, the locking mechanism may be of the same type as described with respect to FIG. 5.

Figure 7:
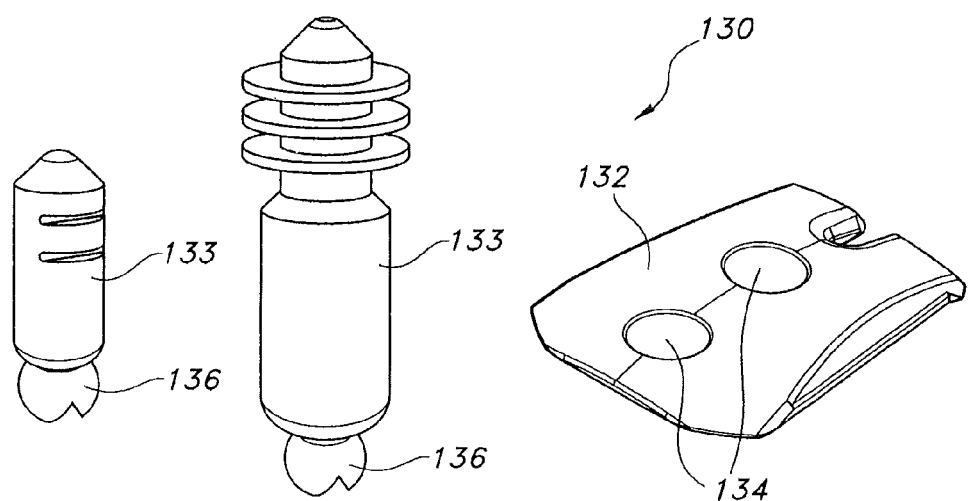
FIG. 7 is an illustration of a base of the glenoid assembly according to another embodiment of the present invention.

Turning now to FIG. 7, another embodiment of the present invention will be shown. In this embodiment, a modular base 130 is included. The modular base 130 includes a support base 132 and a plurality of glenoid attachment members 133. The support base 132 includes attachment mechanisms 134. In this case, the attachment mechanisms 134 are generally spherical recesses. The glenoid attachment members 133 also include attachment mechanisms 136. In this embodiment, the attachment mechanisms are generally spherical shaped balls that lock into the recesses on the support base 132. Other types of attachment mechanisms may be used. Also, any number and type of glenoid attachment members 133 may be included, such as wedge-shaped fillers, screws, pins, spikes, and other numbers and types of pegs. The base 130 will lock into an articulating member 14, 64, 102 as described above in reference to FIGS. 1-6.

All of the pieces described above may be made of polyethylene, such as ultrahigh molecular weight polyethylene. Other biocompatible plastics may also be used. In some embodiments, biocompatible metals may also be used. In other embodiments, some of the parts, such as the articulation member may be made of biocompatible metal while other parts, such as the base may be made of biocompatible plastics. In other words, any combination of biocompatible plastics and/or metals may be used.

Figure 8:
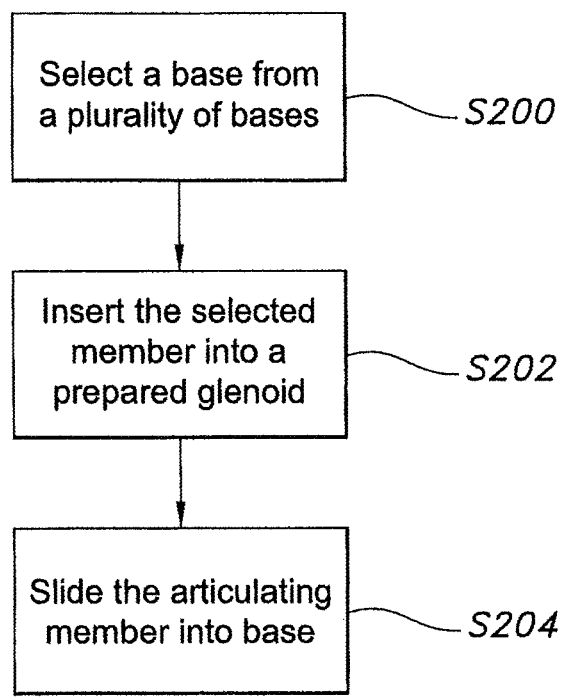
FIG. 8 is a flow chart illustrating a method for assembling the modular glenoid assembly according to one embodiment of the present invention.

Turning now to FIG. 8, a method for using a modular glenoid according to one embodiment of the present invention will be described. First, at step s200, a base is selected from a plurality of bases. Then, at step s202, the selected base is inserted into the prepared glenoid. An articulating member is then slid into the base, locking the articulating member to the base (step s204).

The invention claimed is:

1. The method of assembling a glenoid assembly, the method comprising:
    selecting a base from a plurality of bases, wherein at least one of the plurality of bases has a size different than a size of one of the other of the plurality of bases, each of the plurality of bases having an articulating-member facing side and a glenoid attachment side, wherein each of the plurality of glenoid attachment sides include at least one glenoid attachment member extending outwardly and sized and shaped to extend into a patient's glenoid, wherein the glenoid attachment member of one of the plurality of bases differs from the glenoid attachment member of at least one other of the plurality of bases, and wherein each of the plurality of bases includes a locking mechanism sized and shaped to lock each of the plurality of bases to the articulating member, wherein the plurality of bases includes at least one finned peg and one wedge-shaped filler;
    coupling the selected base to an articulating member; and
    locking the selected base to the articulating member via a locking mechanism.

2. The method of claim 1, wherein the locking mechanism includes a lip on one of the selected base and the articulating member and a recess on the other of the selected base and the articulating member.

3. The method of claim 1, wherein the locking mechanism includes a pair of protrusions on one of the selected base and the articulating member and a pair of recesses on the other of the selected base and the articulating member.

4. The method of claim 1, further comprising inserting the selected base into a prepared glenoid.

5. The method of claim 4, wherein the inserting the selected base into the prepared glenoid is performed before the selected base is coupled to the articulating member.

* * * * *